United States Patent
Nakano et al.

(10) Patent No.: US 10,172,390 B2
(45) Date of Patent: Jan. 8, 2019

(54) NON-COMBUSTION-TYPE FLAVOR INHALER

(71) Applicant: JAPAN TOBACCO INC., Tokyo (JP)

(72) Inventors: Takuma Nakano, Tokyo (JP); Manabu Yamada, Tokyo (JP); Manabu Takeuchi, Tokyo (JP); Hirofumi Matsumoto, Tokyo (JP); Takeshi Shinkawa, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 15/222,648

(22) Filed: Jul. 28, 2016

(65) Prior Publication Data

US 2016/0331040 A1   Nov. 17, 2016

Related U.S. Application Data

(63) Continuation of application No. PCT/JP2015/052171, filed on Jan. 27, 2015.

(30) Foreign Application Priority Data

Jan. 29, 2014   (JP) ................. 2014-014205

(51) Int. Cl.
*H01R 13/62* (2006.01)
*A24F 47/00* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .................................... A24F 47/008
(Continued)

(56) References Cited

U.S. PATENT DOCUMENTS

| | | | |
|---|---|---|---|
| 2008/0092912 A1 | 4/2008 | Robinson et al. | |
| 2010/0242974 A1* | 9/2010 | Pan | A24F 47/008 131/273 |

(Continued)

FOREIGN PATENT DOCUMENTS

| | | |
|---|---|---|
| EP | 0 845 220 A1 | 6/1998 |
| JP | 2010-506594 A | 3/2010 |

(Continued)

OTHER PUBLICATIONS

International Search Report for PCT/JP2015/052171 dated Apr. 21, 2015.

*Primary Examiner* — Tulsidas C Patel
*Assistant Examiner* — Peter G Leigh
(74) *Attorney, Agent, or Firm* — Birch, Stewart, Kolasch & Birch, LLP

(57) ABSTRACT

A non-combustion-type flavor inhaler includes a shape extending from a non-mouthpiece end to a mouthpiece end in a predetermined direction. The non-combustion-type flavor inhaler includes: an aerosol source generating aerosol; an atomizer atomizing the aerosol source without combustion; a power source supplying electric power to the atomizer; and a controller controlling an electric energy supplied from the power source to the atomizer. The controller randomly controls the electric energy supplied to the atomizer.

20 Claims, 10 Drawing Sheets

(51) Int. Cl.
 *A61M 15/06* (2006.01)
 *A61M 11/04* (2006.01)
 *B65B 69/00* (2006.01)
 *H05B 37/02* (2006.01)
 *A61M 16/00* (2006.01)

(52) U.S. Cl.
 CPC ..... *B65B 69/0033* (2013.01); *H05B 37/0227* (2013.01); *A61M 2016/0021* (2013.01); *A61M 2016/0027* (2013.01); *A61M 2205/3375* (2013.01); *A61M 2205/3653* (2013.01); *A61M 2205/584* (2013.01); *A61M 2205/8206* (2013.01)

(58) Field of Classification Search
 USPC ........................................................ 131/329
 See application file for complete search history.

(56) References Cited

U.S. PATENT DOCUMENTS

| | | | | |
|---|---|---|---|---|
| 2011/0226236 A1* | 9/2011 | Buchberger | ......... | A61M 11/041 128/200.23 |
| 2011/0303231 A1* | 12/2011 | Li | ........................ | A24F 47/008 131/329 |
| 2012/0199663 A1* | 8/2012 | Qiu | ....................... | A61M 11/041 239/8 |
| 2012/0204889 A1* | 8/2012 | Xiu | ....................... | A24F 47/008 131/273 |
| 2013/0068225 A1* | 3/2013 | Nichols | ................. | A61M 16/16 128/203.26 |
| 2013/0284192 A1* | 10/2013 | Peleg | .................... | A24F 47/002 131/329 |
| 2013/0319439 A1* | 12/2013 | Gorelick | ............... | A24F 47/008 131/329 |
| 2013/0319440 A1* | 12/2013 | Capuano | ............... | A24F 47/008 131/329 |
| 2014/0014126 A1* | 1/2014 | Peleg | .................... | A24F 47/008 131/329 |

FOREIGN PATENT DOCUMENTS

| | | |
|---|---|---|
| WO | WO 97/48293 A1 | 12/1997 |
| WO | WO 2012/109371 A2 | 8/2012 |
| WO | WO 2013/098398 A2 | 7/2013 |

\* cited by examiner

FIG. 4

| PUFF STATE | PUFF STATE #1 | NON-PUFF STATE #2 | PUFF STATE #2 | NON-PUFF STATE #3 | PUFF STATE #3 | NON-PUFF STATE #4 | PUFF STATE #4 |
|---|---|---|---|---|---|---|---|
| LIGHT-EMITTING MODE | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #1 |

| PUFF STATE | NON-PUFF STATE #5 | PUFF STATE #5 | NON-PUFF STATE #6 | PUFF STATE #6 | NON-PUFF STATE #7 | PUFF STATE #7 | NON-PUFF STATE #8 | PUFF STATE #8 | NON-PUFF STATE #9 OR MORE | PUFF STATE #9 OR MORE |
|---|---|---|---|---|---|---|---|---|---|---|
| LIGHT-EMITTING MODE | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-3 | LIGHT-EMITTING MODE #1 | LIGHT-EMITTING MODE #2-3 | LIGHT-EMITTING MODE #1 | EMISSION END MODE | LIGHT-EMITTING MODE #1 |

FIG. 5

| PUFF STATE | NON-PUFF STATE #1 | PUFF STATE #1 | NON-PUFF STATE #2 | PUFF STATE #2 | NON-PUFF STATE #3 | PUFF STATE #3 | NON-PUFF STATE #4 | PUFF STATE #4 |
|---|---|---|---|---|---|---|---|---|
| LIGHT-EMITTING MODE | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 |

| PUFF STATE | NON-PUFF STATE #5 | PUFF STATE #5 | NON-PUFF STATE #6 | PUFF STATE #6 | NON-PUFF STATE #7 | PUFF STATE #7 | NON-PUFF STATE #8 | PUFF STATE #8 | NON-PUFF STATE #9 OR MORE | PUFF STATE #9 OR MORE |
|---|---|---|---|---|---|---|---|---|---|---|
| LIGHT-EMITTING MODE | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-3 | LIGHT-EMITTING MODE #1-3 | LIGHT-EMITTING MODE #2-3 | LIGHT-EMITTING MODE #1-3 | EMISSION END MODE | LIGHT-EMITTING MODE #1-4 |

NON-COMBUSTION-TYPE FLAVOR INHALER

CROSS REFERENCE TO RELATED APPLICATIONS

This application is a Continuation of PCT International Application No. PCT/JP2015/052171, filed on Jan. 27, 2015, which claims priority under 35 U.S.C. 119(a) to Patent Application No. 2014-014205, filed in Japan on Jan. 29, 2014, all of which are hereby expressly incorporated by reference into the present application.

TECHNICAL FIELD

The present invention relates to a non-combustion-type flavor inhaler including a shape extending from a non-mouthpiece end to a mouthpiece end in a predetermined direction.

BACKGROUND ART

Conventionally, a non-combustion-type flavor inhaler for inhaling a flavor without combustion has been known. The non-combustion-type flavor inhaler includes a shape extending from a non-mouthpiece end to a mouthpiece end in a predetermined direction. The non-combustion-type flavor inhaler includes an aerosol source that generates aerosol, a heat source that heats the aerosol source without combustion, and a power source that supplies electric power to the heat source (for example, refer to Patent Literature 1).

For typical cigarettes that generate aerosol with combustion, various types of management have been performed in order to inhibit discrepancies in smoke flavor between individuals. However, there are slight discrepancies in smoke flavor between individuals.

Meanwhile, the electric power that has been determined constantly and uniquely is supplied to the above non-combustion-type flavor inhaler. Thus, the above non-combustion-type flavor inhaler is designed so that there are hardly discrepancies in smoke flavor. Therefore, the above non-combustion-type flavor inhaler does not intend to reproduce a sense of use of a typical cigarette (fluctuations in smoke flavor).

CITATION LIST

Patent Literature

Patent Literature 1: JP 2010-506594 A

SUMMARY

A first feature is summarized as a non-combustion-type flavor inhaler having a shape extending from a non-mouthpiece end to a mouthpiece end in a predetermined direction, comprising: an aerosol source generating aerosol; an atomizer atomizing the aerosol source without combustion; a power source supplying electric power to the atomizer; and a controller controlling an electric energy supplied from the power source to the atomizer, wherein the controller randomly controls the electric energy supplied to the atomizer.

A second feature is summarized as the non-combustion-type flavor inhaler according to the first feature 1, wherein the controller increases the electric energy supplied to the atomizer from a reference electric energy in a stepwise manner in accordance with an increase of a number of times of puff actions of inhaling the aerosol, and the controller randomly controls the reference electric energy.

A third feature is summarized as the non-combustion-type flavor inhaler according to the first feature, wherein in a case where the power source of the non-combustion-type flavor inhaler is deactivated in a first on-state where a power source of the non-combustion-type flavor inhaler is turned on, the controller randomly controls an electric energy supplied to the atomizer in a second on-state based on an electric energy that is supplied to the atomizer in the first on-state, the second on-state defined by a state where the power source of the non-combustion-type flavor inhaler is turned on again before a stationary time exceeds a predetermined stationary time, the stationary time defined by a time that is passed after deactivation of the power source of the non-combustion-type flavor inhaler.

A fourth feature is summarized as the non-combustion-type flavor inhaler according to the third feature, wherein a range of possible values for the electric energy supplied to the atomizer in the second on-state is narrower than a range of possible values for the electric energy to be supplied to the atomizer in the first on-state.

A fifth feature is summarized as the non-combustion-type flavor inhaler according to the first feature, wherein the controller controls: a standard mode applied to a user whose time required for one puff action of inhaling the aerosol is within a standard required time section period; and a shortening mode applied to a user whose time required for one puff action of inhaling the aerosol is shorter than the standard required time section period, in one puff action in the standard mode, the controller controls the power source so as to supply a standard electric energy to the atomizer during a section before a first time is passed, and controls the power source so as to supply an electric energy smaller than the standard electric energy to the atomizer during a section after the first time is passed, in one puff action in the shortening mode, the controller controls the power source so as to supply a first electric energy larger than the standard electric energy to the atomizer during a section before a second time is passed, controls the power source so as to supply a second electric energy smaller than the first electric energy to the atomizer during a section before a third time is passed after the second time, and controls the power source so as to supply an electric energy smaller than the second electric energy to the atomizer during a section after the third time is passed, and the controller randomly controls the standard electric energy.

A sixth feature is summarized as the non-combustion-type flavor inhaler according to the first feature, wherein the controller controls a first mode in which a first reference electric energy is used as the reference electric energy, and a second mode in which a second reference electric energy larger than the first reference electric energy is used as the reference electric energy.

A seventh feature is summarized as the non-combustion-type flavor inhaler according to the second feature, wherein the controller controls the power source so as to supply an electric energy smaller than the reference electric energy to the atomizer when the puff action is performed after a number of times of puff actions is exceeded a predetermined number of times.

An eighth feature is summarized as the non-combustion-type flavor inhaler according to the seventh feature, wherein the controller turns the power source of the non-combustion-type flavor inhaler off when a certain period of time is passed after the number of puff actions is exceeded a predetermined number of times.

A ninth feature is summarized as the non-combustion-type flavor inhaler according to the second feature, wherein the controller increases a gradient of the electric energy supplied to the atomizer in accordance with the increase of the number of times of puff actions of inhaling the aerosol.

A tenth feature is summarized as the non-combustion-type flavor inhaler according to the fifth feature, wherein the controller sets the standard mode or the shortening mode based on learning of a puff action of a user.

An eleventh second feature is summarized as the non-combustion-type flavor inhaler according to the fifth feature, wherein the controller sets the standard mode or the shortening mode by operation of a user.

BRIEF DESCRIPTION OF DRAWINGS

FIG. 4 is an exemplary table of a light-emitting mode according to the first embodiment.

FIG. 5 is another exemplary table of a light-emitting mode according to the first embodiment.

DESCRIPTION OF EMBODIMENTS

Next, an embodiment will be described. Note that, the same or similar portions are denoted with the same or similar reference signs in the descriptions of the drawings below. Note that, the drawings are schematic and a ratio of each size is different from a real one.

Therefore, specific sizes and the like should be judged in consideration of the following descriptions. Needless to say, portions of which relationship and ratios of mutual sizes are different between the mutual drawings, are included.

[Summary of Embodiments]

A non-combustion-type flavor inhaler according to an embodiment includes a shape extending from a non-mouthpiece end to a mouthpiece end in a predetermined direction. The non-combustion-type flavor inhaler includes an aerosol source generating aerosol, an atomizer atomizing the aerosol source without combustion, a power source supplying an electric power to the atomizer, and a controller controlling an electric energy supplied from the power source to the atomizer. The controller randomly controls the electric energy supplied to the atomizer.

According to the embodiment, the controller randomly controls the electric energy supplied to the atomizer. Accordingly, a sense of use of a typical cigarette generating aerosol with combustion (fluctuations in smoke flavor) can be reproduced. A sense of use similar to a typical cigarette can be achieved.

[First Embodiment]
(Non-combustion-type Flavor Inhaler)

Figure 1:
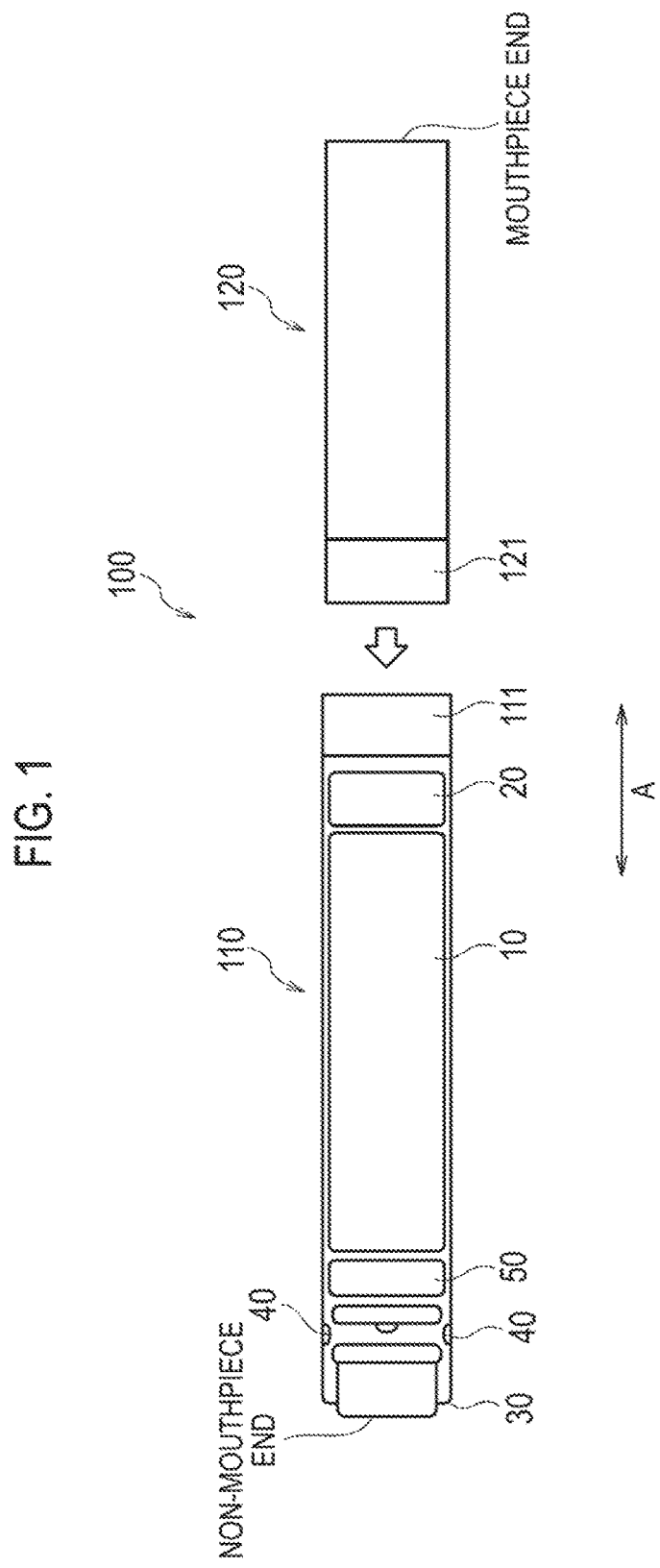
FIG. 1 is a view of a non-combustion-type flavor inhaler 100 according to a first embodiment.
Figure 2:
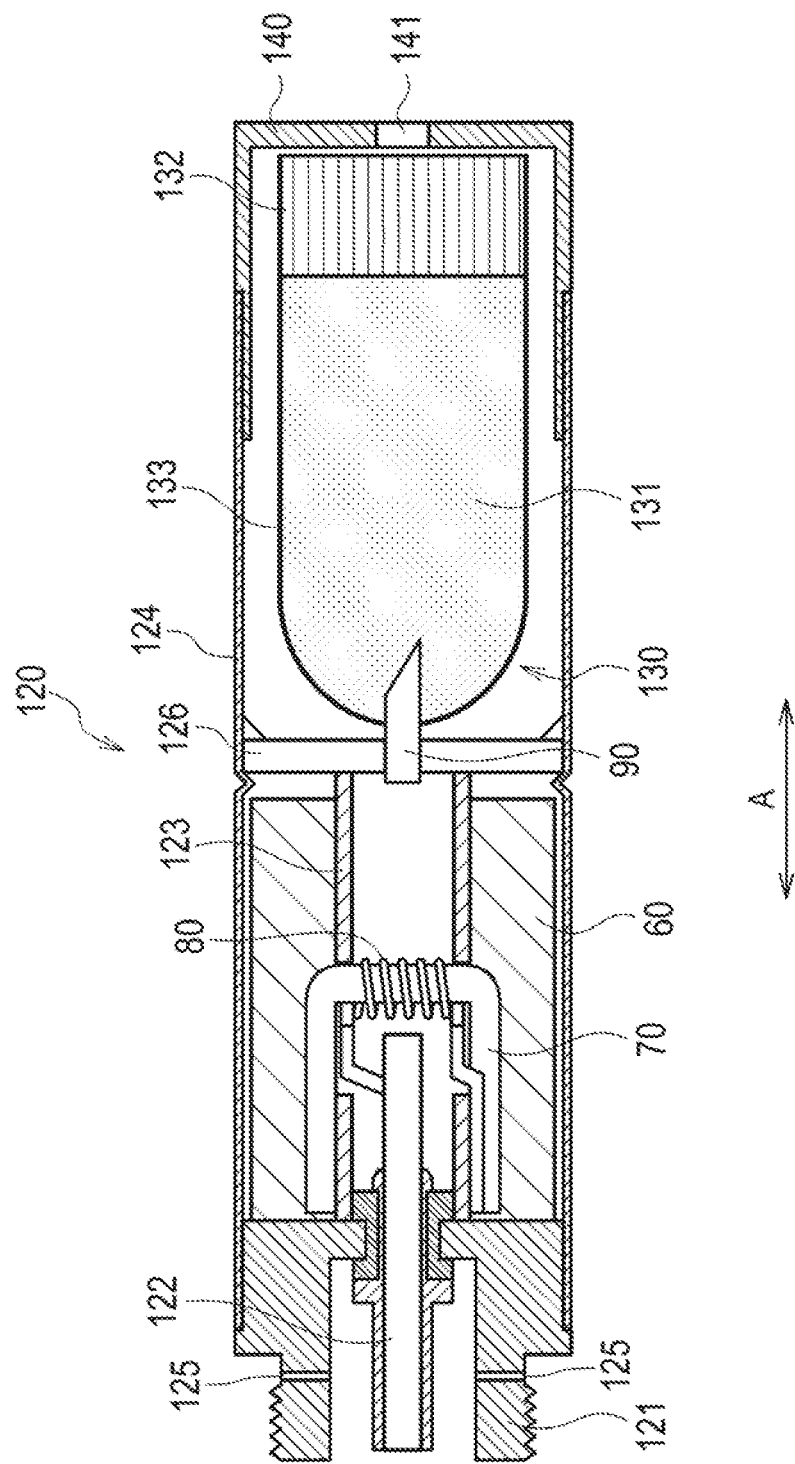
FIG. 2 is view of an atomizing unit 120 according to the first embodiment.

A non-combustion-type flavor inhaler according to a first embodiment will be described below. FIG. 1 is a view of the non-combustion-type flavor inhaler 100 according to the first embodiment. FIG. 2 is a view of an atomizing unit 120 according to the first embodiment.

According to the first embodiment, the non-combustion-type flavor inhaler 100 is an instrument for inhaling a flavor without combustion, and includes a shape extending in a predetermined direction A that is a direction from a non-mouthpiece end to a mouthpiece end.

As illustrated in FIG. 1, the non-combustion-type flavor inhaler 100 includes an electric component unit 110 and an atomizing unit 120. The electric component unit 110 includes a female connector 111 which is provided to a portion adjacent to the atomizing unit 120. The atomizing unit 120 includes a male connector 121 which is provided to a portion adjacent to the electric component unit 110. The female connector 111 includes a spiral groove extending in a direction perpendicular to the predetermined direction A. The male connector 121 includes a spiral protrusion extending in a direction perpendicular to the predetermined direction A. Screwing the female connector 111 and the male connector 121 couples the atomizing unit 120 and the electric component unit 110. The atomizing unit 120 is configured to be attachable to and to be detachable from the electric component unit 110.

The electric component unit 110 includes a power source 10, a sensor 20, a push button 30, a light-emitting element 40, and a control circuit 50.

The power source 10 is, for example, a lithium ion battery. The power source 10 supplies an electric power necessary for an action of the non-combustion-type flavor inhaler 100. For example, the power source 10 supplies the electric power to the sensor 20, the light-emitting element 40, and the control circuit 50. The power source 10 also supplies the electric power to a heat source 80 to be described later.

The sensor 20 detects wind pressure caused by an inhaling action of a user. Specifically, the sensor 20 detects negative pressure caused when air is inhaled toward the atomizing unit 120. The sensor 20 includes, but is not particularly limited to, a piezoelectric element.

The push button 30 is configured to be pressed to the side of the mouthpieces end in the predetermined direction A. For example, predetermined operation of the push button 30 (operation, such as continuously pressing over the predetermined number of times) turns a power source of the non-combustion-type flavor inhaler 100 on. When the operation of the push button 30 turns the power source on, the power source 10 supplies the electric power to the control circuit 50 and then, the electric power is supplied to the sensor 20 and the light-emitting element 40 through the control circuit 50. Here, note that the power supply to the heat source 80 is performed when the power source is turned on and also the sensor 20 detects the inhaling action of the user. That is, in a non-puff state where aerosol has not been inhaled, the power supply to the heat source 80 is not performed.

Alternatively, predetermined operation of the push button 30 (operation such as pressing and holding the push button 30 down) may turn the power source of the non-combustion-type flavor inhaler 100 off. The predetermined operation of the push button 30 turns the power source of the non-combustion-type flavor inhaler 100 off. Thus, power consumption can be reduced when the non-combustion-type flavor inhaler 100 has not been used.

The push button 30 may be configured to perform at least one of a turn-on and a turn-off of the power source of the non-combustion-type flavor inhaler 100.

The light-emitting element 40 is a light source, such as an LED or an electric light. The light-emitting element 40 is provided on a side wall extending in the predetermined direction. The light-emitting element 40 is preferably provided in proximity to the non-mouthpiece end. Accordingly, the user can easily view a light-emitting pattern of the light emitting element 40 during the inhaling action in comparison to a case where a light-emitting element is provided in proximity to the non-mouthpiece end on an axial line in the predetermined direction A. The light-emitting pattern of the light-emitting element 40 is a pattern that notifies the user of a state of the non-combustion-type flavor inhaler 100.

The control circuit 50 controls an action of the non-combustion-type flavor inhaler 100. Specifically, the control circuit 50 controls the light-emitting pattern of the light-emitting element 40, and controls the electric power supplied to the heat source 80.

As illustrated in FIG. 2, the atomizing unit 120 includes a holder 60, an absorber 70, the heat source 80, and a destroying portion 90. The atomizing unit 120 includes a capsule unit 130 and a mouthpiece unit 140. Here, the atomizing unit 120 includes an air introducing hole 125 for introducing external air to the inside, an air channel 122 interconnecting with the electric component unit 110 (the sensor 20) through the male connector 121, and a ceramic 123 disposed so as to be tubular. The atomizing unit 120 includes a tubular outer wall 124 forming an outer form of the atomizing unit 120. A space surrounded by the ceramic 123 forms an air channel. The ceramic 123 includes, for example, alumina as a main component.

The holder 60 includes a tubular shape and holds an aerosol source that generates aerosol. The aerosol source is a liquid, such as glycerin or propylene glycol. The holder 60 includes, for example, a porous body impregnated with the aerosol source. The porous body is, for example, a resin web.

According to the first embodiment, the above ceramic 123 is disposed inside the holder 60, and inhibits volatilization of the aerosol source held by the holder 60.

The absorber 70 is provided to be adjacent to the holder 60, and includes a substance that absorbs the aerosol source from the holder 60. The absorber 70 includes, for example, a glass fiber.

The heat source 80 heats the aerosol source without combustion. The heat source 80 is, for example, a heating wire wound around the absorber 70. The heat source 80 heats the aerosol source absorbed by the absorber 70.

The destroying portion 90 is a member for destroying a part of a predetermined film 133 in a state where the capsule unit 130 has been attached. According to the embodiment, the destroying portion 90 is held by a partition wall member 126 for partitioning the atomizing unit 120 and the capsule unit 130. The partition wall member 126 is, for example, a polyacetal resin. The destroying portion 90 is, for example, a cylindrical hollow needle extending in the predetermined direction A. Puncturing the predetermined film 133 with a leading end of the hollow needle, destroys the part of the predetermined film 133. A space inside the hollow needle forms an air channel interconnecting the atomizing unit 120 and the capsule unit 130 so that air passes through the air channel. Here, a mesh having a degree of roughness through which a raw material included in a flavor source 131 does not pass, is preferably provided inside the hollow needle. The roughness of the mesh is, for example, in a range of from 80 to 200 mesh.

In this case, a depth of the hollow needle that penetrates into the capsule unit 130 is preferably in a range of from 1.0 to 5.0 mm, more preferably, in a range of 2.0 to 3.0 mm. Accordingly, portions except the predetermined portion of the predetermined film 133 is prevented from being destroyed. Thus, an escape of the flavor source 131 to be filled in a space partitioned by the predetermined film 133 and a filter 132, can be inhibited. Separation of the hollow needle from the space is inhibited. Thus, an appropriate air channel from the hollow needle to the filter 132 can be preferably retained.

A sectional area of the vertical needle is preferably in a range of from 2.0 to 3.0 mm² in a section perpendicular to the predetermined direction A. Accordingly, the flavor source 131 is inhibited from falling from the capsule unit 130 when the hollow needle is extracted.

The leading end of the hollow needle preferably has a slant angled from 30° to 45° with respect to a direction perpendicular to the predetermined direction A.

Note that the embodiment is not limited to this. The destroying portion 90 may be a portion adjacent to the predetermined film 133 in a state where the capsule unit 130 has been attached. The user may pressurize this type of portion so that a part of the predetermined film 133 may be destroyed.

The capsule unit 130 is configured to be attachable to and detachable from a main body unit. The capsule unit 130 includes the flavor source 131, the filter 132, and the predetermined film 133. The flavor source 131 is filled in the space partitioned by the predetermined film 133 and the filter 132. Here, the main body unit is a unit including portions except the capsule unit 130. For example, the main body unit includes the electric component unit 110, the holder 60, the absorber 70, and the heat source 80 described above.

The flavor source 131 is provided on the side of the mouthpiece end beyond the holder 60 holding the aerosol source, and generates a flavor to be inhaled by the user together with the aerosol generated from the aerosol source. Here, note that the flavor source 131 includes a solid substance so as to be prevented from flowing out from the space partitioned by the predetermined film 133 and the filter 132. Examples of the flavor source 131 that can be used include shredded tobacco, a formed body including a tobacco raw material formed granular, a formed body including the tobacco raw material formed to have a sheet in shape. The flavor source 131 may include a plant, such as mint or a herb, except tobacco. A flavor, such as menthol, may be added to the flavor source 131.

Note that in a case where the flavor source 131 includes the tobacco raw material, the tobacco raw material is apart from the heat source 80. Thus, there is no need for heating the tobacco raw material, and the flavor can be inhaled. In other words, note that inhalation of an unnecessary substance caused by heating the tobacco raw material is inhibited.

According to the first embodiment, the amount of the flavor source 131 to be filled in the space partitioned by the filter 132 and the predetermined film 133, is preferably in a range of from 0.15 to 1.00 g/cc. An occupancy rate of the volume of occupancy of the flavor source 131 in the space partitioned by the filter 132 and the predetermined film 133, is preferably in a range of from 50 to 100%. Note that the volume of the space partitioned by the filter 132 and the predetermined film 133, is preferably in a range of from 0.6 to 1.5 ml. Accordingly, while maintaining an appropriate size, the capsule unit 130 can house the flavor source 131 so that the user can sufficiently taste the flavor.

In a state where the destroying portion 90 has destroyed the part of the predetermined film 133, and the atomizing unit 120 and the capsule unit 130 have been interconnected with each other, entire ventilation resistance of the capsule unit 130 (a pressure drop) is preferably in a range of from 10 to 100 mmAq, more preferably, in a range of from 20 to 90 mmAq in a case where air is inhaled with a flow rate of 1050 cc/min from a leading end portion of the capsule unit 130 (a portion to be destroyed) to a rear end of the filter 132. Setting the ventilation resistance of the flavor source 131 in the above preferable range inhibits an phenomenon in which the flavor source 131 excessively filters the aerosol. Thus, the flavor can be effectively supplied to the user. Note that 1 mmAq is equivalent to 9.80665 Pa. Thus, the above ventilation resistance can be expressed by Pa.

The filter 132 is provided adjacent to the side of the mouthpiece end with respect to the flavor source 131, and includes a substance having breathability. For example, the filter 132 is preferably an acetate filter. The filter 132 preferably has a degree of roughness through which the raw material included in the flavor source 131 does not pass.

Ventilation resistance of the filter 132 is preferably in a range of from 5 to 20 mmAq. Accordingly, while effectively adsorbing a vapor component occurring from the flavor source 131, the filter 132 can allow the aerosol to pass therethrough and can supply an appropriate flavor to the user. In addition, an appropriate sense of air resistance can be given to the user.

A ratio between mass of the flavor source 131 and mass of the filter 132 (a mass ratio) is preferably in a range of from 3:1 to 20:1, more preferably, in a range of from 4:1 to 6:1.

The predetermined film 133 is integrally formed with the filter 132, and includes a member having no breathability. The predetermined film 133 covers portions except a portion adjacent to the filter 132, on an outer surface of the flavor source 131. The predetermined film 133 includes at least one compound selected from the group consisting of gelatin, polypropylene, and polyethylene terephthalate. Gelatin, polypropylene, polyethylene, and polyethylene terephthalate have no breathability, and are suitable for forming a thin film. In addition, gelatin, polypropylene, polyethylene, and polyethylene terephthalate have resistance sufficient to moisture contained in the flavor source 131. Polypropylene, polyethylene, and polyethylene terephthalate particularly have exceptional water resistance. Furthermore, since having basic resistance, gelatin, polypropylene, and polyethylene barely degrade due to a basic component even in a case where the flavor source 131 has the basic component.

The thickness of the predetermined film 133 is preferably in a range of from 0.1 to 0.3 μm. Accordingly, the part of the predetermined film 133 can be easily destroyed with a function for protecting the flavor source 131 by the predetermined film 133, retained.

As described above, the predetermined film 133 is integrally formed with the filter 132. For example, the predetermined film 133 is adhered to the filter 132 with glue or the like. Alternatively, in a direction perpendicular to the predetermined direction A, an outer form of the predetermined film 133 may be made so as to be smaller than an outer form of the filter 132. The filter 132 may be put into the predetermined film 133. Restoring force of the filter 132 may fit the filter 132 into the predetermined film 133. Alternatively, an engaging portion for engaging the predetermined film 133 may be provided to the filter 132.

Here, a shape of the predetermined film 133 preferably includes, but is not particularly limited to, a recess shape in a section perpendicular to the predetermined direction A. In this case, after the flavor source 131 is filled into the inside of the predetermined film 133 having the recess shape, the filter 132 closes an opening of the predetermined film 133 into which the flavor source 131 has been filled.

In a case where the predetermined film 133 has the recess shape, in the section perpendicular to the predetermined direction A, a maximum sectional area (namely, a sectional area of the opening to which the filter 132 is fit) is preferably in a range of from 25 to 80 mm$^2$, more preferably, in a range of from 25 to 55 mm$^2$ in a sectional area of a space surrounded by the predetermined film 133. In this case, in the section perpendicular to the predetermined direction A, a sectional area of the filter 132 is preferably in a range of from 25 to 55 mm$^2$. The thickness of the filter 132 in the predetermined direction A is preferably in a range of from 3.0 to 7.0 mm.

The mouthpiece unit 140 includes a mouthpiece hole 141. The mouthpiece hole 141 is an opening from which the filter 132 is exposed. The user inhales the aerosol from the mouthpiece hole 141 to inhale the flavor together with the aerosol.

According to the first embodiment, the mouthpiece unit 140 is configured so as to be attachable to and detachable from the outer wall 124 of the atomizing unit 120. For example, the mouthpiece unit 140 has a cup-shape configured to fit to an inner surface of the outer wall 124. However, the embodiment is not limited to this. The mouthpiece unit 140 may be attached to the outer wall 124 by a hinge or the like so as to be turnable.

According to the first embodiment, the mouthpiece unit 140 is provided as a body separated from the capsule unit 130. That is the mouthpiece unit 140 is included in a part of the main body unit. However, the embodiment is not limited to this. The mouthpiece unit 140 may be integrally provided with the capsule unit 130. In this case, note that the mouthpiece unit 140 is included in a part of the capsule unit 130.

(Control Circuit)

Figure 3:
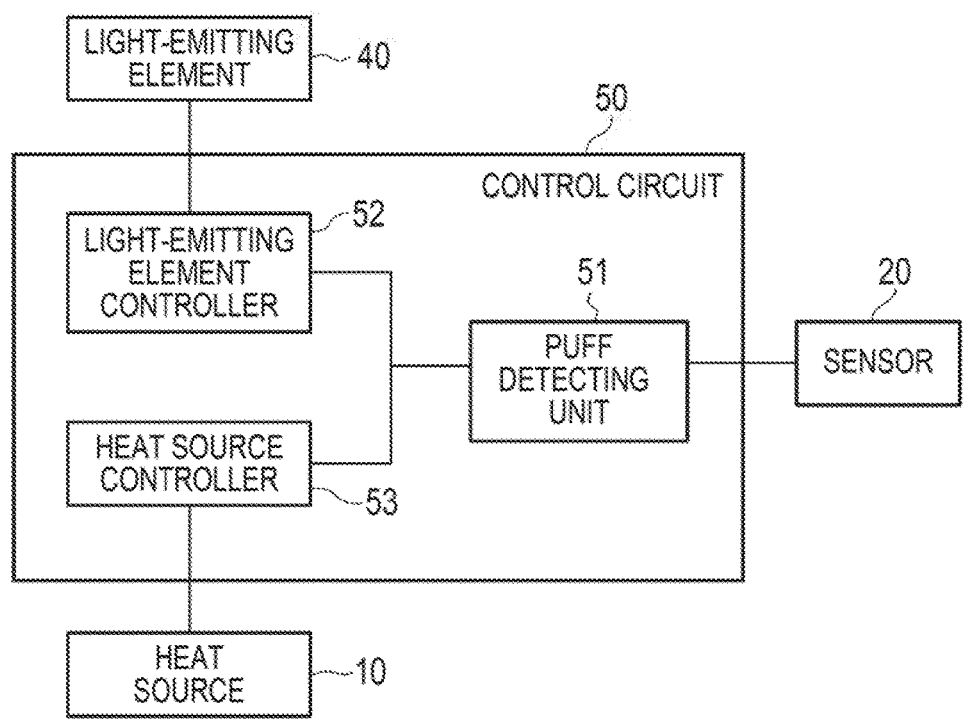
FIG. 3 is a block diagram of a control circuit 50 according to the first embodiment.

A control circuit according to the first embodiment will be described below. FIG. 3 is a block diagram of the control circuit 50 according to the first embodiment.

As illustrated in FIG. 3, the control circuit 50 includes a puff detector 51, a light-emitting element controller 52, and a heat source controller 53.

The puff detector 51 is connected to the sensor 20 that detects wind pressure caused by the inhaling action of the user. The puff detector 51 detects a puff state based on a detection result of the sensor 20 (for example, negative pressure in the non-combustion-type flavor inhaler 100). In detail, the puff detector 51 detects a puff state where the aerosol has been being inhaled and a puff state where the aerosol has been being inhaled. Accordingly, the puff detector 51 can specify the number of times of puff actions of inhaling the aerosol. The puff detector 51 can detect a time period required for one puff action of inhaling the aerosol.

The light-emitting element controller 52 is connected to the light-emitting element 40 and the puff detector 51, and controls the light-emitting element 40. Specifically, the light-emitting element controller 52 controls the light-emitting element 40 in a first light-emitting mode in a puff state where the aerosol has been being inhaled. Meanwhile, the light-emitting element controller 52 controls the light-emitting element 40 in a second light-emitting mode different from the first light-emitting mode, in a non-puff state where the aerosol has not been inhaled.

Here, the light-emitting mode is defined by a combination of parameters, such as the amount of light of the light-emitting element 40, the number of light-emitting elements 40 in a lighting state, a color of the light-emitting element 40, and a cycle in which lighting of the light-emitting element 40 and non-lighting of the light-emitting element 40 repeat. The different light-emitting mode means that at least any one of the above parameters is different.

According to the first embodiment, the second light-emitting mode varies in response to the number of times of puff actions of inhaling the aerosol. The first light-emitting mode may vary in response to the number of times of puff actions of inhaling the aerosol, or may be constant, being independent of the number of times of puff actions of inhaling the aerosol.

For example, the first light-emitting mode is a mode in which a red light-emitting element 40 lights in order to be made similar to a sense of use of a typical cigarette generating aerosol with combustion. The first light-emitting mode is preferably a mode in which the light-emitting element 40 has continuously lighted. Alternatively, the first light-emitting mode may be a mode in which lighting of the light-emitting element 40 and non-lighting of the light-emitting element 40 repeat in a first cycle.

For example, the second light-emitting mode is a mode in which a blue light-emitting element 40 lights in order to notify the user that the aerosol resource has not been heated. The second light-emitting mode may be a mode in which lighting of the light-emitting element 40 and non-lighting of the light-emitting element 40 repeat in a second cycle longer than the first cycle.

As described above, the second light-emitting mode varies in response to the number of times of puff actions of inhaling the aerosol.

For example, the second light-emitting mode may be a mode in which the number of light-emitting elements 40 to be controlled increases in accordance with an increase of the number of times of puff actions. For example, the light-emitting element controller 52 controls one light-emitting element 40 in the second light-emitting mode in a first puff action, and controls two light-emitting elements 40 in the second light-emitting mode in a second puff action. Alternatively, the light-emitting element controller 52 controls n light-emitting elements 40 in the second light-emitting mode in a first puff action, and controls n−1 light-emitting elements 40 in the second light-emitting mode in a second puff action.

Alternatively, the second light-emitting mode may be a mode in which the amount of light of a light-emitting element 40 increases or decreases in accordance with an increase of the number of times of puff actions. Alternatively, the second light-emitting mode may be a mode in which a color of a light-emitting element 40 varies in accordance with an increase of the number of times of puff actions.

Note that, even in a case where the first light-emitting mode varies in response to the number of puff actions, a variation in the first light-emitting mode is basically similar to a variation in the second light-emitting mode in terms of a manner.

According to the first embodiment, in a case where the number of times of puff actions of inhaling the aerosol has reached a predetermined number of times (for example, eight times), the light-emitting element controller 52 completes the control according to the first light-emitting mode and the second light-emitting mode, and then controls the light-emitting element 40 in a emitting end mode.

The emitting end mode may be a mode in which a timing to complete a puff action is notified to the user, and is preferably different from the first light-emitting mode and the second light-emitting mode. For example, the emitting end mode is a mode in which the amount of light of the light-emitting element 40 is smaller than those in the first light-emitting mode and the second light-emitting mode, and in which the amount of light of the light-emitting element 40 gradually decreases.

The heat source controller 53 is coupled to the power source 10, and controls the electric energy supplied from the power source 10 to the heat source 80. The electric energy is a multiplication result of time period and electric power (depending on voltage or current), and is a value that is controlled by time period and electric power. For example, the heat source controller 53 controls a voltage applied from the power source 10 to the heat source 80 by controlling DC-DC converter and the like disposed with the power source 10.

First, the heat source controller 53 increases the electric energy supplied to the heat source 80 from a reference electric energy in a stepwise manner in accordance with an increase of the number of times of puff actions of inhaling the aerosol. Accordingly, similarity to a sense of use of a typical cigarette generating aerosol with combustion, can be achieved. In this case, the heat source controller 53 randomly controls the reference electric energy supplied to the heat source 80. The heat source controller 53 randomly determines the reference electric energy using predetermined random numbers and the like so that a standard deviation of the total amount of supply of the aerosol (the total amount of TPM) becomes ±20% per puff action series. A variation range of the electric energy can be appropriately changed based on a composition of the aerosol resource and a structure of the atomizing unit. For example, in a case where glycerin is used as the aerosol source in the flavor inhaler illustrated in FIG. 1, when the reference power is randomly determined so as to be in a range of ±10% of predetermined power, the standard deviation of the total amount of supply of the aerosol (the total amount of TPM) per puff action series can be in a range of ±20%. Timing at which the reference electric energy is randomly determined, may be timing at which the power source of the non-combustion-type flavor inhaler 100 is turned on, or may be timing at which a puff action series described later (a series of actions of repeating a puff action the predetermined number of times) is performed the predetermined number of times.

Here, the heat source controller 53 may control the power source 10 so that the electric energy smaller than the reference electric energy is supplied to the heat source 80, in a case where a puff action has been performed after the number of times of puff actions has exceeded the predetermined number of times. Accordingly, even in a case of timing at which a puff action should be completed, the user can inhale a slight amount of aerosol. Thus, a sense of satisfaction of the user can increase.

The heat source controller 53 turns the power source of the non-combustion-type flavor inhaler 100 off when a predetermined time has passed after the number of times of puff actions has exceeded a predetermined number of times. Accordingly, power waste of the non-combustion-type flavor inhaler 100 in accordance with a case where turning off the power source of the non-combustion-type flavor inhaler 100 has been omitted, is inhibited.

Here, with a combination of the above actions, the heat source controller 53 may supply the electric energy smaller than the reference electric energy to the heat source 80 after the number of times of puff actions has exceeded a predetermined number of times, and may turn the power source of the non-combustion-type flavor inhaler 100 off after the number of times of puff actions has exceeded the predetermined number of times and after a predetermined time has passed.

The power source of the non-combustion-type flavor inhaler 100 may be independent of the control of the heat source controller 53 and may be compulsorily turned off by predetermined operation of the push button 30 (operation, such as pressing and holding the push button 30). In other words, the power source of the non-combustion-type flavor inhaler 100 may be compulsorily turned off by the predetermined operation of the push button 30 (the operation, such as pressing and holding the push button 30) even before the number of times of puff actions reaches the predetermined number of times.

The heat source controller 53 preferably increases a gradient of the electric energy supplied to the heat source 80 in accordance with an increase of the number of times of puff actions of inhaling the aerosol. Here, the gradient of electric power is defined by the number of times of puff actions in which constant power is retained, and by an amount of increase in which the power increases. That is, the number of times of puff actions in which the constant power is retained decreases in accordance with the increase of the number of times of puff actions. Alternatively, the amount of increase in which the power increases, increases in accordance with the increase of the number of times of puff actions. Alternatively, the number of times of puff actions in which the constant power is retained decreases and also the amount of increase in which the power increases, increases in accordance with the increase of the number of times of puff actions.

Furthermore, the heat source controller 53 may control a first mode in which a first reference electric energy is used as the reference electric energy, and may control a second mode in which a second reference electric energy larger than the first reference electric energy is used as the reference electric energy. As the reference electric energy, the reference electric energies with three steps or more steps may be provided. In this case, switching of the reference electric energy may be performed by operation of the push button 30. For example, pressing down the push button 30 one time may apply the first mode and pressing down twice may apply the second mode. The push button 30 may be replaced with a touch sensor. These operations may turn the power source of the non-combustion-type flavor inhaler 100 on. That is, turning the power source on and switching the reference electric energy may be performed by one action with operation of the push button 30. Note that an action for turning the power source on with operation of the push button 30 on may separate from an action for switching the reference electric energy.

Secondly, the heat source controller 53 controls a standard mode applied to a user whose time required for one puff action of inhaling the aerosol is within a standard required time section, and controls a shortening mode applied to a user whose time required for one puff action of inhaling the aerosol is shorter than the standard required time section. Here, the standard required time section means a time section during which a balance of the amount of supply of the aerosol (TPM: the amount of Total Particulate Matter) is particularly excellent.

Specifically, in one puff action in the standard mode, the heat source controller 53 controls the power source 10 to supply a standard electric energy to the heat source 80 during a section before a first time has passed. The heat source controller 53 controls the power source 10 to supply the electric energy smaller than the standard electric energy to the heat source 80 during a section after the first time has passed. During the section after the first time has passed, the heat source controller 53 may immediately drop the electric energy supplied to the heat source 80 zero, or may gradually decrease the electric energy supplied to the heat source 80.

Here, the first time is preferably equivalent to end timing for the above standard required time section. Alternatively, the first time may be longer than the end timing for the standard required time section in a range in which the balance of the amount of supply of the aerosol (the amount of TPM) is allowable.

Meanwhile, in one puff action in the shortening mode, the heat source controller 53 controls the power source 10 so as to supply a first electric energy larger than the standard electric energy to heat source 80 during a section before a second time has passed, so as to supply a second electric energy smaller than the first electric energy to the heat source 80 during a section before a third time has passed after the second time, and so as to supply an electric energy smaller than the second electric energy to the heat source 80 during a section after the third time has passed. During a section after the third time has passed, the heat source controller 53 may immediately drop the electric energy supplied to the heat source 80 zero, or may gradually decrease the electric energy supplied to the heat source 80.

The second time is preferably earlier than start timing for the above standard required time section. Alternatively, the second time may be included in the standard required time section, or may be later than the end timing for the standard required time section. The third time is preferably equivalent to the end timing for the above standard required time section. Alternatively, the third time may be later than the end timing for the standard required time section in a range in which the balance of the amount of supply of the aerosol (the amount of TPM) is allowable.

The second electric energy smaller than the first electric energy may be equivalent to the standard electric energy described above. Alternatively, the second electric energy may be larger than the standard electric energy, or may be smaller than the standard electric energy.

As described above, the heat source controller 53 increases the electric energy applied to the heat source 80 from the reference electric energy in a stepwise manner in accordance with the increase of the number of times of puff actions. In other words, note that the standard electric energy in one puff action is synonymous with the reference electric energy described above, and increases in accordance with the increase of the number of times of puff actions.

That is, the heat source controller 53 randomly controls the standard electric energy (=the reference electric energy) supplied to the heat source 80. As described above, the heat source controller 53 randomly determines the reference electric energy using the predetermined random numbers and the like so that the standard deviation of the total amount of supply of the aerosol (the total amount of TPM) becomes ±20% per puff action series. Timing for randomly determining the standard electric energy, may be timing at which the power source of the non-combustion-type flavor inhaler 100 is turned on, or may be timing at which a puff action series to be described later (a series of actions of repeating a puff action the predetermined number of times) is performed the predetermined number of times.

The heat source controller 53 may set the standard mode or the shortening mode based on learning of a puff action of the user. In detail, the heat source controller 53 sets the standard mode in a case where a time required for one puff action, acquired based on the learning is within the standard required time section. The heat source controller 53 sets the shortening mode in a case where the time required for one puff action, acquired based on the learning is shorter than the standard required time section.

According to the first embodiment, the atomizing unit 120 is attachable to and detachable from the electric component unit 110. The capsule unit 130 is attachable to and detachable from the main body unit including the electric component unit 110. In other words, the electric component unit 110 can be reused through a plurality of times of puff action series. The puff action series is a series of actions of repeating the predetermined number of times of puff actions. Therefore, the standard mode or the shortening mode may be set in a second and later puff action series, by learning a time required for one puff action in a first puff action series. Alternatively, the standard mode or the shortening mode may be set in n+1 (or n+2)-th and later puff action by learning a time required for one puff action in initial n puff actions per puff action series.

Alternatively, the heat source controller 53 may set the standard mode or the shortening mode by operation of the user. In this case, a switch for switching between the standard mode and the shortening mode is provided in the non-combustion-type flavor inhaler 100. Note that switching between the standard mode and the shortening mode may be allowed per puff action series. Alternatively, the switching between the standard mode and the shortening mode may not be allowed and a mode that has been initially set may be stationary applied per puff action series.

(Light-emitting Mode)

An exemplary light-emitting mode according to the first embodiment will be described below. FIGS. 4 and 5 are examples of the light-emitting mode according to the first embodiment. FIGS. 4 and 5 illustrate an exemplary case where the user should basically complete a puff action series in a case where the number of times of puff actions has reached eight times (the predetermined number of times).

First, a first example of the light-emitting mode will be described with reference to FIG. 4. As illustrated in FIG. 4, a first light-emitting pattern in puff states is independent of the number of times of puff actions, and is constant. Meanwhile, a second light-emitting pattern in non-puff states varies depending on the number of times of puff actions.

For example, as illustrated in FIG. 4, a light-emitting mode #2-1 is used as the second light-emitting mode in non-puff states #1 to #4. A light-emitting mode #2-2 is used as the second light-emitting mode in non-puff states #5 to #7. A light-emitting mode #2-3 is used as the second light-emitting mode in non-puff state #8. Note that the emitting end mode described above is used in a ninth and later non-puff states.

Meanwhile, a light-emitting mode #1 is used as the first light-emitting mode in puff states #1 to #8. In a ninth and later puff states, the light-emitting mode #1 may be also used as the first light-emitting mode. Alternatively, in order to indicate a puff that has exceeded eight times (the predetermined number of times), mutual different light-emitting modes may be used for the first light-emitting mode and the second light-emitting mode.

The light-emitting modes #1, #2-1, #2-2, #2-3, and the emitting end mode are mutually different light-emitting modes. As described above, the light-emitting mode is defined by a combination of parameters, such as the amount of light of the light-emitting element 40, the number of light-emitting elements 40 in a lighting state, a color of the light-emitting element 40, a cycle in which lighting of the light-emitting element 40 and non-lighting of the light-emitting element 40 repeat. The different light-emitting mode means at least any one of the above parameters is different.

For example, the light-emitting mode #1 is preferably a light-emitting mode that images combustion, in order to be made similar to a sense of use of a typical cigarette generating aerosol with combustion. The light-emitting mode #2-1 is preferably a light-emitting mode that images an early stage of a puff action series. The light-emitting mode #2-2 is preferably a light-emitting mode that images a middle state of the puff action series. The light-emitting mode #2-3 is preferably a light-emitting mode that images a final stage of the puff action series. The emitting end mode is preferably a mode that notifies the user of the effect that it is time to complete a puff action.

Secondly, the first example of the light-emitting mode will be described with reference to FIG. 5. As illustrated in FIG. 5, the first light-emitting pattern in puff states and the second light-emitting pattern in non-puff states both vary in response to the number of times of puff actions.

For example, as illustrated in FIG. 5, the light-emitting modes #2-1, #2-2, and #2-3 are used as the second light-emitting mode in non-puff states in a manner similar to the case illustrated in FIG. 4.

Meanwhile, a light-emitting mode #1-1 is used as the first light-emitting mode in puff states #1 to #4. A light-emitting mode #1-2 is used as the first light-emitting mode in puff states #5 to #7. A light-emitting mode #1-3 is used as the first light-emitting mode in a puff state #8. Note that a light-emitting mode #1-4 is used in a ninth and later puss states.

The light-emitting mode #1-1 is preferably a light-emitting mode that images an early stage of a puff action series. The light-emitting mode #1-2 is preferably a light-emitting mode that images a middle stage of the puff action series. The light-emitting mode #1-3 is preferably a light-emitting mode that images a final stage of the puff action series. Note that the light-emitting mode #1-4 is preferably a mode that notifies the user of the effect that it is time to complete a puff action, similarly to the emitting end mode.

According to the first embodiment, as illustrated in FIGS. 4 and 5, a case where a light-emitting mode in a non-puff state #1 (namely, a non-puff state immediately after the power source of the non-combustion-type flavor inhaler 100 has been turned on) is the second light-emitting mode (the light-emitting mode #2-1), has been exemplified. However, the embodiment is not limited to this. The light-emitting mode in the non-puff state #1 may be a start light-emitting mode different from the second light-emitting mode. The start light-emitting mode is preferably is a mode that notifies the user of the effect that it is ready to start a puff action.

(Power Control in Puff Action Series)

An exemplary power control in a puff action series according to the first embodiment will be described below.

Figure 6:
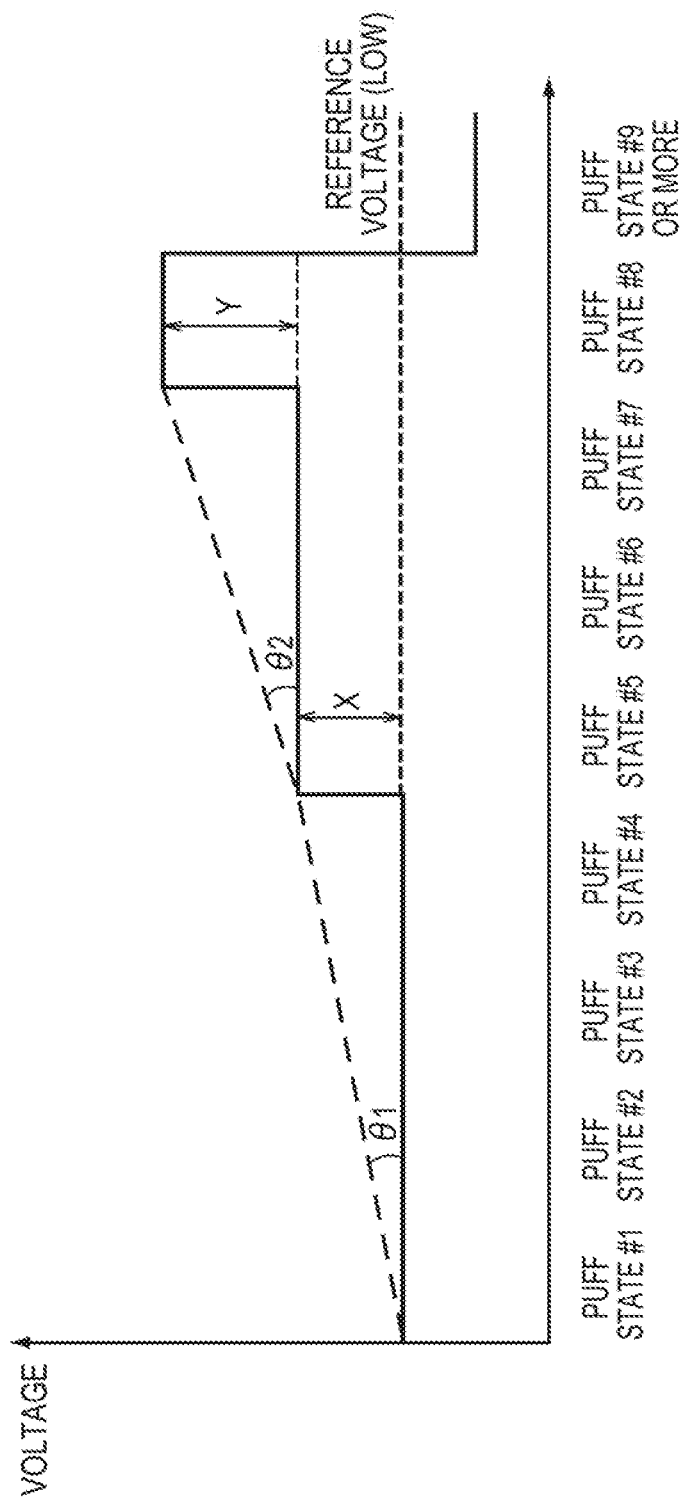
FIG. 6 is a graphical representation of exemplary power control in a puff action series according to the first embodiment.
Figure 7:
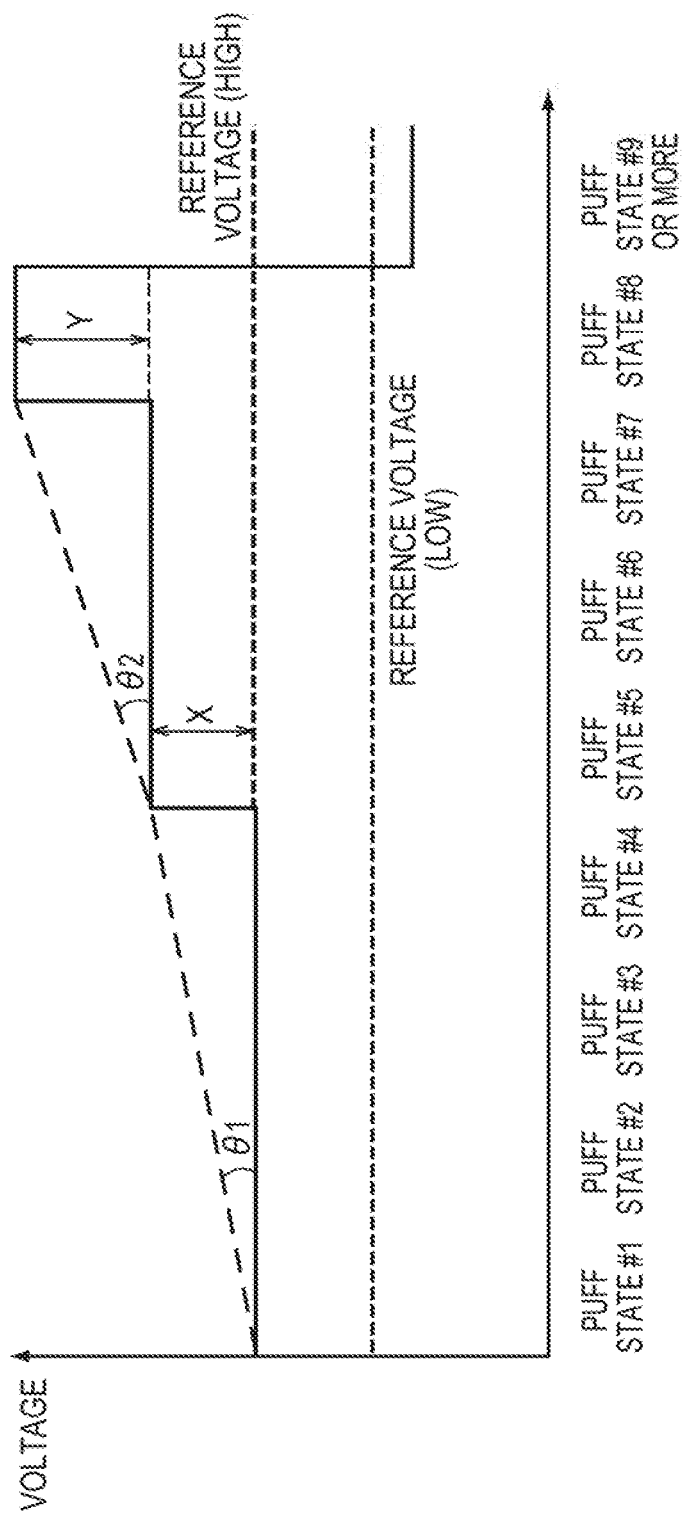
FIG. 7 is a graphical representation of other exemplary power control in a puff action series according to the first embodiment.

FIGS. 6 and 7 are examples of the power control in the puff action series according to the first embodiment. FIGS. 6 and 7 illustrate an exemplary case where the user should basically complete the puff action series when the number of times of puff actions has reached eight times (the predetermined number of times). The electric power is not supplied to the heat source 80 in a non-puff state. Thus, in FIGS. 6 and 7, behavior of supply of the power is omitted in the non-puff state.

Here, a case where the electric energy be applied to the heat source 80 controls by a voltage supplied to the heat source 80, will be exemplified. Therefore, according to the first embodiment, it may be thought that the electric energy is synonymous with the voltage. FIG. 6 illustrates a first mode (Low mode) in which a first voltage is used as a reference voltage. FIG. 7 illustrates a second mode (High mode) in which a second voltage higher than the first voltage is used as a reference voltage. Note that, although the reference voltages are different from each other, behavior of a voltage applied to the heat source 80 is the same in the first mode (Low mode) and the second mode (High mode).

As illustrated in FIGS. 6 and 7, the heat source controller 53 increases the voltage applied to the heat source 80 from the reference voltage in a stepwise manner in accordance with an increase of the number of times of puff actions of inhaling the aerosol. Specifically, in puff states #1 to #4, the voltage applied to the heat source 80 is constant and the reference voltage is applied to the heat source 80. In puff states #5 to #7, the voltage applied to the heat source 80 is constant and the voltage higher than the reference voltage by one step is applied to the heat source 80. A voltage higher than the reference voltage by two steps is applied to the heat source 80 in a puff state #8. A voltage lower than the reference voltage is applied to the heat source 80 in a ninth and later puff states.

As described above, the heat source controller 53 increases a gradient of the voltage applied to the heat source 80 in accordance with the increase of the number of times of puff actions of inhaling the aerosol.

For example, the number of times of puff actions in which a constant voltage is retained decreases in accordance with the increase of the number of times of puff actions. That is, the number of times of puff actions in which the reference voltage is applied is four times, the number of time of puff actions in which the voltage higher than the reference voltage by the one step is applied is three times, and the number of times of puff actions in which the voltage higher than the reference voltage by the two steps is applied is once. Alternatively, the number of times of puff actions in which the constant voltage is retained decreases in accordance with the increase of the number of times of puff actions. Alternatively, an amount of increase Y of the second voltage is larger than an amount of increase X of the voltage at the first step.

Accordingly, gradients of the voltage (θ1 and θ2) defined by the number of times of puff actions in which a constant voltage is retained and by the amount of increase in which the voltage increases in accordance with an increase of a number of times of puff actions. In other words, the gradient θ2 at a middle stage of the puff action series is larger than the gradient θ1 at an early stage of the puff action series.

In FIGS. 6 and 7, the number of steps at which the voltage applied to the heat source 80 increases, is two steps. The embodiment is not limited to this. The number of steps at which the voltage to be applied to the heat source 80 increases, may be three steps or more. Alternatively, the number of steps at which the voltage to be applied to the heat source 80 increases, may be one step.

(Power Control in One Puff Action)

Figure 8:
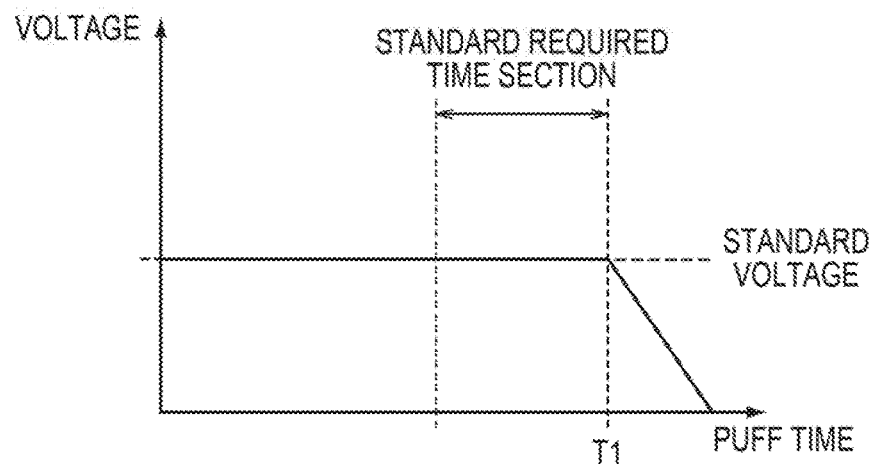
FIG. 8 is a graphical representation of exemplary power control in one puff action according to the first embodiment.
Figure 9:
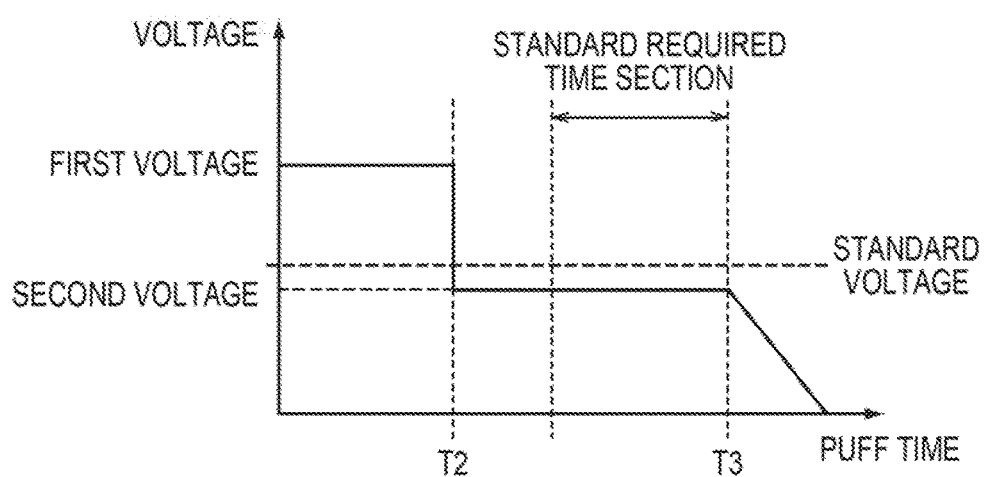
FIG. 9 is a graphical representation of other exemplary power control in one puff action according to the first embodiment.

An exemplary power control in one puff action according to the first embodiment will be described below. FIGS. 8 and 9 are examples of the power control in one puff action according to the first embodiment. FIGS. 8 and 9 illustrate a exemplary case where the user should basically complete a puff action series in a case where the number of times of puff actions has reached eight times (the predetermined number of times).

Here, a case where the electric energy supplied to the heat source 80 controls by a voltage applied to the heat source 80, will be exemplified. Therefore, according to the first embodiment, it may be thought that the electric energy is synonymous with the voltage. FIG. 8 illustrates behavior of the voltage applied to the heat source 80 in the standard mode. FIG. 9 illustrates behavior of the voltage applied to the heat source 80 in the shortening mode.

As illustrated in FIG. 8, in the standard mode, a standard voltage is applied to the heat source 80 during a section before the first time T1 has passed. A voltage smaller than the standard voltage is applied to the heat source 80 during a section after the first time T1 has passed.

Here, a case where the first time T1 is equivalent to the end timing of the standard required time section, is exemplified. Note that, as described above, the first time T1 is not limited to this.

As illustrated in FIG. 9, in the shortening mode, the first voltage higher than the standard voltage is applied to the heat source 80 during a section before the second time T2 has passed. The second voltage lower than the first voltage is applied to the heat source 80 during a section before the third time T3 has passed after the second time T2. A voltage smaller than the second voltage is applied to the heat source 80 during a section after the third time T3 has passed.

Here, a case where the second time is earlier than the start timing of the standard required time section, is exemplified. A case where the third time is equivalent to the end timing of the standard required time section, is exemplified. A case where the second voltage is lower than the standard voltage, is exemplified. Note that, as described above, the second time T2, the third time T3, and the second voltage are not limited to these example.

Note that, in a case where the standard mode or the shortening mode has been set, it can be thought that a time required for one puff action varies. Even in this case, note that a profile of the voltage illustrated in FIG. 8 or 9 is traced and the voltage becomes zero together with completion of the puff action. In other words, the electric energy supplied to the heat source is at least controlled in accordance with action modes that have been previously determined. Thus, note that there is no need for complicated control of continuing to control the amount of electric power based on an air flow (the amount of inhale) during a period in which the electric power has been being supplied to the heat source 80.

(Functions and Effects)

According to the first embodiment, the heat source controller 53 randomly controls the electric energy supplied to the heat source 80 (the reference electric energy or the standard electric energy). Accordingly, a sense of use of a typical cigarette generating aerosol with combustion (fluctuations in smoke flavor) can be reproduced. A sense of use similar to a typical cigarette can be achieved.

According to the first embodiment, the light-emitting element controller 52 controls the light-emitting element 40 in the second light-emitting mode different from the first light-emitting mode in the non-puff state where the aerosol has not been inhaled. Accordingly, the user can grasp whether the non-combustion-type flavor inhaler 100 is available, even in the non-puff state. The light-emitting mode in the puff state is different from the light-emitting mode in the non-puff state. Thus, a sense of use similar to a sense of use of a typical cigarette generating aerosol with combustion, can be achieved.

According to the first embodiment, the second light-emitting mode varies in response to the number of times of puff actions of inhaling the aerosol. Accordingly, the user can easily grasp a puff progressing state, based on the variation of the second light-emitting mode, in the non-puff state where emission of light of the light-emitting element 40 is easily viewed.

According to the first embodiment, the heat source controller 53 increases the electric energy supplied to the heat source 80 from the reference electric energy in a stepwise manner in accordance with an increase of the number of times of puff actions of inhaling the aerosol. Accordingly, the amount of supply of the aerosol can come close to a typical cigarette generating aerosol with combustion. Thus, a sense of use similar to the typical cigarette can be achieved.

According to the first embodiment, the heat source controller 53 controls: the first mode in which the first reference electric energy is used as the reference electric energy; and the second mode in which the second reference electric energy larger than the first reference electric energy is used as the reference electric energy. Accordingly, the user can select the amount of aerosol in response to users' preference with one non-combustion-type flavor inhaler 100.

According to the first embodiment, for even a user whose time required for one puff action is shorter than the standard required time, with introduction of the shortening mode, increasing the temperature of the heat source faster than that in the standard mode can improve a degree of satisfaction of the user. The electric energy supplied to the heat source decreases during a section after the first time or the third time has passed, independent of the action modes. Thus, inhaling a decomposed substance is inhibited and degradation in smoke flavor is inhibited.

According to the first embodiment, the action modes that have been predetermined (the standard mode and the shortening mode) may be prepared. The electric energy supplied to the heat source may be controlled in accordance with the action modes that have been predetermined. Accordingly, during supplied the electric power to the heat source 80, there is no need for complicated control of continuing to control the amount of the electric power based on an air flow (the amount of inhale). In other words, improvement of degradation in smoke flavor and satisfaction of the user can be achieved with a simple configuration.

According to the first embodiment, the push button 30 for turning the power source of the non-combustion-type flavor inhaler 100 on or off is provided. The user can deliberately start or complete a puff action series. Thus, a sense of use similar to a typical cigarette generating aerosol with combustion (a sense of period of the puff action series) can be achieved in comparison to a case where the push button 30 is not provided.

According to the first embodiment, the push button 30 for turning the power source of the non-combustion-type flavor inhaler 100 off is provided. Thus, there is no need for supplying the power to the sensor 20 and the light-emitting element 40 when the non-combustion-type flavor inhaler 100 has not been used, and power consumption can be reduced. Meanwhile, even in a case where the push button 30 is provided in order to reduce the power consumption, the user can grasp whether the power source of the non-combustion-type flavor inhaler 100 has been turned on, with the light-emitting mode of the light-emitting element 40. In detail, the light-emitting element 40 emits light even in the non-puff state in addition to the puff state. Thus, when the light-emitting element 40 has emitted light, it can be grasped that the non-combustion-type flavor inhaler 100 has been turned on. When the light-emitting element 40 has not emitted light, it can be grasped that the power source of the non-combustion-type flavor inhaler 100 has been turned off.

[First Modification]

A first modification of the first embodiment will be described below. Differences from the first embodiment will be mainly described below.

Specifically, according to the first embodiment described above, the heat source controller 53 controls the electric energy supplied from the power source 10 to the heat source 80 by controlling a voltage which is applied from the power source 10 to the heat source 80. In detail, the heat source controller 53 increases the electric energy (voltage) supplied to the heat source 80 from the reference electric energy (reference voltage) in a stepwise manner in accordance with an increase of the number of times of puff actions of inhaling the aerosol (refer to FIG. 7).

In contrast, according to the first modification, a heat source controller 53 controls a voltage applied from the power source 10 to the heat source 80 by pulse control. The heat source controller 53 controls the electric energy supplied from the power source 10 to the heat source 80 by control of a pulse width (a duty ratio) of the voltage applied to the heat source 80. In detail, the heat source controller 53 shortens the pulse width of the voltage applied to the heat source 80 from a reference pulse width in a stepwise manner in accordance with an increase of the number of times of puff actions of inhaling aerosol (refer to FIG. 10).

Figure 10:
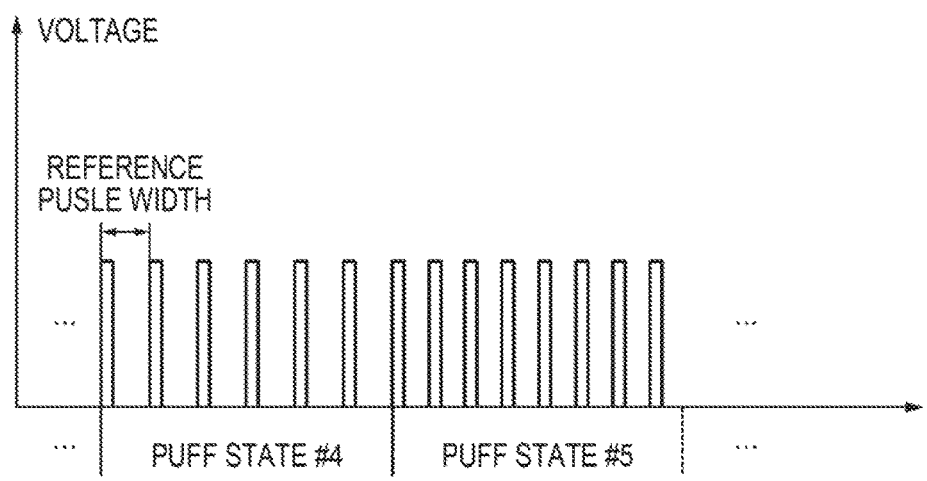
FIG. 10 is a graphical representation of exemplary power control in a puff action series according to a first modification.

FIG. 10 illustrates an exemplary case where the electric energy increases between a puff state #4 and a puff state #5, by following the example illustrated in FIG. 7. In FIG. 10, puff states except the puff state #4 and the puff state #5 have been omitted. Needless to say, the control of the pulse width (the duty ratio) acquires an effect similar to that in the example illustrated in FIG. 7.

[Second Modification]

A second modification of the first embodiment will be described below. Differences from the first embodiment will be mainly described below.

Specifically, according to the first embodiment described above, the heat source controller 53 controls the electric energy supplied from the power source 10 to the heat source 80 by controlling a voltage applied from the power source 10 to the heat source 80. In detail, the heat source controller 53 increases the electric energy (voltage) supplied to the heat source 80 from the reference electric energy (reference voltage) in a stepwise manner in accordance with an increase of the number of times of puff actions of inhaling the aerosol (refer to FIG. 7).

Figure 11:
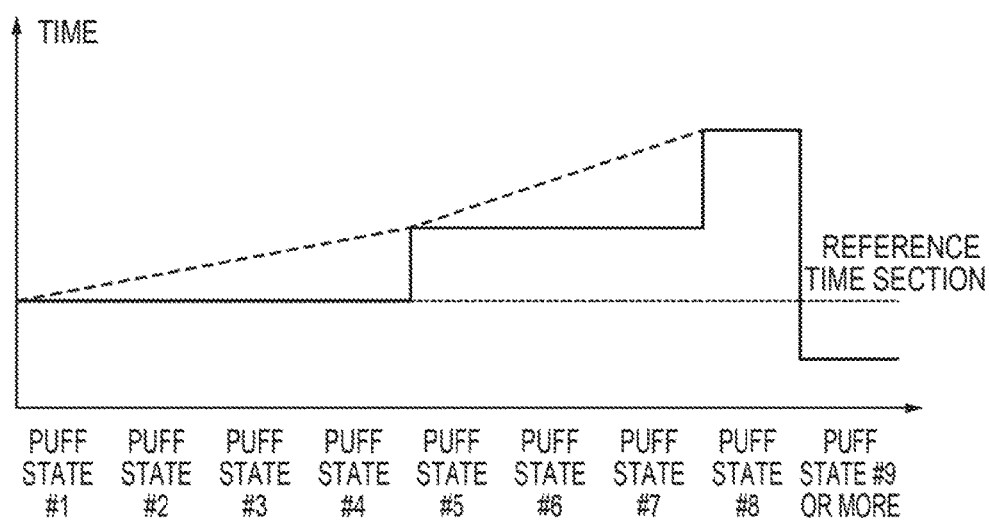
FIG. 11 is a graphical representation of exemplary power control in a puff action series according to a second modification.

In contrast, according to the second modification, a heat source controller 53 controls the electric energy supplied from a power source 10 to a heat source 80 by controlling a time period during which a voltage is applied to the heat source 80. In detail, the heat source controller 53 increases the time period during which the voltage is applied to the heat source 80 from a reference time period in a stepwise manner in accordance with an increase of the number of times of puff actions of inhaling aerosol (refer to FIG. 11).

According to the second modification, the reference time period means a maximum time period during which application of the voltage to the heat source 80 continues, in a case where a user continues a puff action. Therefore, when a time period during which the user continues the puff action exceeds the reference time period, the application of the voltage to the heat source 80 stops. Note that a first light-emitting mode of a light-emitting element 40 is retained while the puff action of the user continues even when the application of the voltage stops. Accordingly, the total electric energy supplied to the heat source 80 varies in one puff action. Thus, an effect similar to that in the example illustrated in FIG. 7 is acquired.

Note that, in a case where the standard mode and the shortening mode described in the first embodiment are introduced, the first time, the second time, and the third time may be adjusted (prolonged) in accordance with an increase of the number of times of puff actions of inhaling the aerosol.

[Third Modification]

A third modification of the first embodiment will be described below. Differences from the first embodiment will be mainly described below.

Specifically, according to the first embodiment, the heat source controller 53 randomly controls the electric energy supplied to the heat source 80 (the reference electric energy or the standard electric energy). Timing at which the electric energy is randomly determined may be timing at which the power source of the non-combustion-type flavor inhaler 100 is turned on, or may be timing at which a puff action series has been performed a predetermined number of times.

In contrast, according to the third modification, timing at which the electric energy (the reference electric energy or the standard electric energy) is randomly determined, will be described. In detail, as described above, the heat source controller 53 turns the power source of the non-combustion-type flavor inhaler 100 off when a predetermined time has passed after the number of times of puff actions has exceeded a predetermined number of times. According to the third modification, when a time passed from turn-off of the power source of the non-combustion-type flavor inhaler 100 (a stationary time) has exceeded a predetermined stationary time, the heat source controller 53 determines that a puff action series has been completed. In other words, when the power source of the non-combustion-type flavor inhaler 100 is turned on again before the stationary time exceeds the predetermined stationary time, the heat source controller 53 determines that the puff action series has not been completed. Turning the power source on again described above is referred to as "resumption", hereinafter. The heat source controller 53 randomly determines the electric energy (the reference electric energy or the standard electric energy) even in a case of the above resumption.

In the above presupposition, according to the third modification, in a case where the power source of the non-combustion-type flavor inhaler 100 is deactivated in a first on-state where a power source of the non-combustion-type flavor inhaler 100 is turned on, the controller randomly controls an electric energy supplied to the heat source 80 in a second on-state based on an electric energy that is supplied to the heat source 80 in the first on-state, the second on-state defined by a state where the power source of the non-combustion-type flavor inhaler 100 is turned on again before the stationary time exceeds the predetermined stationary time, the stationary time defined by a time that is passed after deactivation of the power source of the non-combustion-type flavor inhaler 100. Here, a range of randomly possible values for the electric energy supplied to the heat source 80 in the on-second state is narrower than a range of randomly possible values for the electric energy supplied to the heat source 80 in the first on-state.

According to the third modification, a case where the heat source controller 53 randomly determines a reference voltage, will be exemplified. The heat source controller 53 randomly determines the reference voltage in accordance with a normal distribution illustrated in FIG. 12, in a case where the power source of the non-combustion-type flavor inhaler 100 has been turned on again after the stationary time has exceeded the predetermined stationary time. A mean value in the normal distribution is u1 and a standard deviation in the normal distribution is σ1 in the normal distribution illustrated in FIG. 12.

Figure 12:
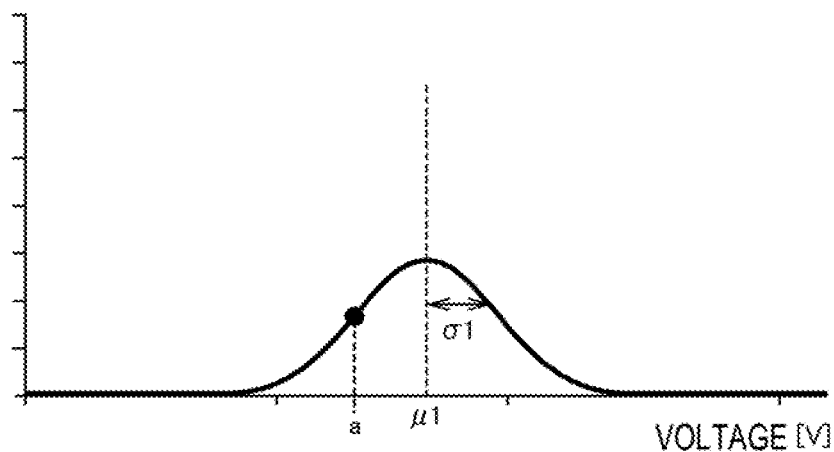
FIG. 12 is a graphical representation of a method of determining reference power according to a third modification.

For example, after "a" has been determined as the reference voltage for n-th puff action series, the heat source controller 53 randomly determines the reference voltage using the normal distribution illustrated in FIG. 12 when (n+1)-th puff action series has started.

Figure 13:
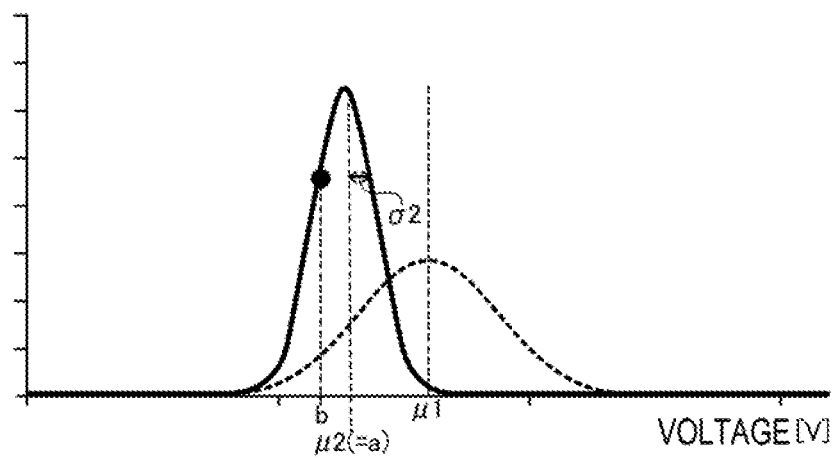
FIG. 13 is a graphical representation of another method of determining reference power according to the third modification.

In contrast, the heat source controller 53 randomly determines the reference voltage in accordance with a normal distribution indicated with a solid line in FIG. 13 in a case where the power source of the non-combustion-type flavor inhaler 100 has been turned on again before the stationary time exceeds the predetermined stationary time. In the normal distribution illustrated in FIG. 13, a mean value of the normal distribution is the reference voltage before the resumption, and a standard deviation of the normal distribution is σ2(<σ1).

For example, after "a" has been determined as a reference voltage for n-th puff action series, the heat source controller 53 has, as the normal distribution, σ2 smaller than σ1 illustrated in FIG. 12, and also randomly determines the reference voltage using the normal distribution having a mean of "a" (refer to FIG. 13), in a case where an n-th puff action series has resumed.

In this manner, when the puff action series resumes, the heat source controller 53 has, as the standard deviation, σ2 smaller than σ1, and also randomly determines the reference voltage using the normal distribution having, as a mean, the reference voltage before the resumption. Therefore, a probability that a reference voltage close to the reference voltage before the resumption is selected, increases. Thus, a possibility that a sense of discomfort is given to the user when the puff action series resumes, is reduced. Determining the reference voltage again when the puff action series resumes, can also reproduce a sense of use of a typical cigarette generating aerosol with combustion (fluctuations in smoke flavor).

According to the third modification, the normal distributions are exemplified as distributions referred when the reference voltage is randomly determined. The embodiment is not limited to this. As a distribution to be referred when the reference voltage is randomly determined, a uniform distribution may be used. In a case where the uniform distribution is used, in resumption timing of the puff action series, a range of the reference voltage selectable is at least narrow with, as a center, the reference voltage before the resumption, in comparison to other timing except the resumption timing of the puff action series.

[Other Embodiments]

The present invention has been described in the above embodiment. The descriptions and the drawings included in a part of this disclosure do not limit the present invention.

The disclosure clarifies various alternative embodiments, examples, and investment techniques for persons skilled in the art.

According to the embodiment, the heat source controller 53 randomly controls the electric energy supplied to the heat source 80 (the reference electric energy or the standard electric energy). The heat source controller 53 may randomly control any power except the reference electric energy or the standard electric energy. For example, the heat source controller 53 may randomly control an amount of increase of the electric energy supplied to the heat source 80 in a case where the electric energy supplied to the heat source 80 increases in a stepwise manner in accordance with an increase of the number of times of puff actions of inhaling the aerosol. Alternatively, the heat source controller 53 may randomly control a gradient of the electric energy supplied to the heat source 80 in an increase of the number of times of puff actions of inhaling the aerosol. As described above, the gradient of electric power is defined by the number of times of puff actions in which constant electric power is retained, and by an amount of increase in which the electric power increases.

According to the embodiment, the number of times of puff actions may be, but has been not particularly referred, corrected with a value (the amount of aerosol generation) defined by a time required for one puff action and the electric energy supplied to the heat source 80. Specifically, the number of times of puff actions may be cumulated by adding a value multiplied by a predetermined coefficient α (α<1) once, in a case where the amount of aerosol generated in one puff action is less than a default value. Meanwhile, the number of times of puff actions may be cumulated by adding a value multiplied by a predetermined coefficient β (β>1) once, in a case where the amount of aerosol generated in one puff action is more than the default value. That is, the number of times of puff actions is not necessarily an integer.

According to the embodiment, timing at which the electric energy supplied to the heat source 80 increases is, but has not been particularly referred, preferably synchronized with timing at which the second light-emitting mode varies, in power control in a puff action series. For example, as illustrated in FIGS. 6 and 7, in a case where the electric energy (voltage) to be supplied to the heat source 80 increases between the puff state #4 and the puff state #5, the second light-emitting mode preferably varies between the puff state #4 and the puff state #5.

According to the embodiment, as illustrated in FIGS. 8 and 9, the voltage smaller than the standard voltage is, but has not been particularly described, applied to the heat source 80 in a section after the first time T1 or third time T3 has passed. The first light-emitting mode preferably continues during such the section.

According to the embodiment, the first mode in which the first reference electric energy is used as the reference electric energy (Low mode illustrated in FIG. 6) and the second mode in which the second reference electric energy larger than the first reference electric energy is used as the reference electric energy (High mode illustrated in FIG. 7), are provided. In this case, a light-emitting mode in the first mode may be different from a light-emitting mode in the second mode. That is, the first light-emitting mode, the second light-emitting mode, and the emitting end mode in the first mode may be different from the first light-emitting mode, the second light-emitting mode, and the emitting end mode in the second mode, respectively.

Switching in a puff action series is, but has not been described in the embodiment in detail, preferably performed as follows:

(a) A case where the power source of the non-combustion-type flavor inhaler 100 is automatically turned off by control of the control circuit 50 when the number of times of puffs reaches a predetermined number of times in the puff action series.

In this case, a new puff action series starts in a case where the power source of the non-combustion-type flavor inhaler 100 has been turned on again.

(b) A case where the power source of the non-combustion-type flavor inhaler 100 is automatically turned off by the control of the control circuit 50 in a case where an inhaling action has not been performed over a certain period of time (for example, the shortest period of time out of "the predetermined number of time×60 sec", "15 min", and "a time during which the number of times of puff actions has exceeded the predetermined number of times and the power source is automatically turned off (namely, the above predetermined time)×2) before the number of times of puffs reaches the predetermined number of times in the puff action series.

In this case, a new puff action series starts in a case where the number of times of puffs has been the number of times of switching determination or more (for example, half the predetermined number of times). Meanwhile, a previous puff action series continues in a case where the number of times of puffs has been less than the number of times of switching determination (for example, half the predetermined number of times).

(c) A case where the predetermined operation of the push button 30 (the operation, such as pressing and holding the push button 30) compulsorily turns the power source of the non-combustion-type flavor inhaler 100 off.

In this case, a new puff action series starts in a case where the power source of the non-combustion-type flavor inhaler 100 has been turned on again. Alternatively, in a case where the power source of the non-combustion-type flavor inhaler 100 has been turned on again, the user may be able to select whether a new puff action series starts or a previous puff action series continues.

Note that in the case (a) or (c) described above, the number of times of puffs to be counted in the puff action series may be reset at timing at which the power source of the non-combustion-type flavor inhaler 100 is turned off. Alternatively, the number of times of puffs to be counted in the puff action series may be reset at timing at which the power source of the non-combustion-type flavor inhaler 100 is turned on again.

Meanwhile, in the case (b), the number of times of puffs to be counted in the puff action series may be reset at timing at which the power source of the non-combustion-type flavor inhaler 100 is turned off in a case where the number of times of puffs has been the number of times of switching determination or more. Alternatively, the number of times of puffs to be counted in the puff action series may be reset at timing at which the power source of the non-combustion-type flavor inhaler 100 is turned on again in a case where the number of times of puffs has been the number of times of switching determination or more. In the case (c) described above, in a case where whether a new puff action series starts or a previous puff action series continues is selectable to the user, the number of times of puffs to be counted in the puff action series may be reset at timing at which the power source of the non-combustion-type flavor inhaler 100 is turned on again and the user makes a selection that a new puff action series starts.

According to the embodiment, a case where the push button 30 is provided as a user interface for turning the power source of the non-combustion-type flavor inhaler 100 on or off, has been exemplified. However, the embodiment is not limited to this. The user interface for turning the power source of the non-combustion-type flavor inhaler 100 on or off may be a hard switch capable of turning the power source of the non-combustion-type flavor inhaler 100 on or off without power consumption.

According to the embodiment, the non-combustion-type flavor inhaler 100 including the push button 30 for turning the power source on, has been described. However, the embodiment is not limited to this. The non-combustion-type flavor inhaler 100 does not necessarily include the push button for turning the power source on. In this case, after the number of times of puffs of the user has exceeded the predetermined number of times in the puff action series and in a case where the predetermined time has passed, the user may be notified of completion of the puff action series only with the emitting end mode of the light-emitting element 40 instead of turning the power source of the non-combustion-type flavor inhaler 100 off according to the embodiment described above. Similarly, instead of turning the power source of the non-combustion-type flavor inhaler 100 off, even when the sensor 20 detects an inhale of the user, energization to the heat source 80 may be controlled so as not to be performed for a certain period of time (for example, for five minutes).

According to the embodiment, the heat source 80 as the atomizer that atomizes the aerosol source without combustion, has been exemplified. The embodiment is not limited to this. The atomizer that atomizes the aerosol source without combustion may be a unit that atomizes the aerosol source with an ultrasonic wave.

Note that the entire disclosure in Japanese Patent Application No. 2014-14205, filed Jan. 29, 2014, is incorporated herein by reference.

INDUSTRIAL APPLICABILITY

According to the embodiment, a non-combustion-type flavor inhaler capable of achieving a sense of use similar to a sense of use of a typical cigarette, can be provided.

The invention claimed is:

1. A non-combustion-type flavor inhaler having a shape extending from a non-mouthpiece end to a mouthpiece end in a predetermined direction, comprising:
   an aerosol source generating aerosol;
   an atomizer atomizing the aerosol source without combustion;
   a power source supplying electric power to the atomizer; and
   a controller controlling an electric energy supplied from the power source to the atomizer,
   wherein the controller randomly controls the electric energy supplied to the atomizer by using random numbers.

2. The non-combustion-type flavor inhaler according to claim 1, wherein
   the controller increases the electric energy supplied to the atomizer from a reference electric energy in a stepwise manner in accordance with an increase of a number of times of puff actions of inhaling the aerosol, and the controller randomly controls the reference electric energy.

3. The non-combustion-type flavor inhaler according to claim 2, wherein
   the controller controls the power source so as to supply an electric energy smaller than the reference electric energy to the atomizer when the puff action is performed after a number of times of puff actions is exceeded a predetermined number of times.

4. The non-combustion-type flavor inhaler according to claim 3, wherein
   the controller turns the power source of the non-combustion-type flavor inhaler off when a certain period of time is passed after the number of puff actions is exceeded a predetermined number of times.

5. The non-combustion-type flavor inhaler according to claim 2, wherein
   the controller increases a gradient of the electric energy supplied to the atomizer in accordance with the increase of the number of times of puff actions of inhaling the aerosol.

6. The non-combustion-type flavor inhaler according to claim 1, wherein
   in a case where the power source of the non-combustion-type flavor inhaler is deactivated in a first on-state where a power source of the non-combustion-type flavor inhaler is turned on, the controller randomly controls an electric energy supplied to the atomizer in a second on-state based on an electric energy that is supplied to the atomizer in the first on-state, the second on-state defined by a state where the power source of the non-combustion-type flavor inhaler is turned on again before a stationary time exceeds a predetermined stationary time, the stationary time defined by a time that is passed after deactivation of the power source of the non-combustion-type flavor inhaler.

7. The non-combustion-type flavor inhaler according to claim 6, wherein
   a range of possible values for the electric energy supplied to the atomizer in the second on-state is narrower than a range of possible values for the electric energy to be supplied to the atomizer in the first on-state.

8. The non-combustion-type flavor inhaler according to claim 1, wherein
   the controller controls: a standard mode applied to a user whose time required for one puff action of inhaling the aerosol is within a standard required time section period; and a shortening mode applied to a user whose time required for one puff action of inhaling the aerosol is shorter than the standard required time section period,
   in one puff action in the standard mode, the controller controls the power source so as to supply a standard electric energy to the atomizer during a section before a first time is passed, and controls the power source so as to supply an electric energy smaller than the standard electric energy to the atomizer during a section after the first time is passed,
   in one puff action in the shortening mode, the controller controls the power source so as to supply a first electric energy larger than the standard electric energy to the atomizer during a section before a second time is passed, controls the power source so as to supply a second electric energy smaller than the first electric energy to the atomizer during a section before a third time is passed after the second time, and controls the power source so as to supply an electric energy smaller than the second electric energy to the atomizer during a section after the third time is passed, and the controller randomly controls the standard electric energy.

9. The non-combustion-type flavor inhaler according to claim 8, wherein
the controller sets the standard mode or the shortening mode based on learning of a puff action of a user.

10. The non-combustion-type flavor inhaler according to claim 8, wherein
the controller sets the standard mode or the shortening mode by operation of a user.

11. The non-combustion-type flavor inhaler according to claim 1, wherein
the controller controls a first mode in which a first reference electric energy is used as the reference electric energy, and a second mode in which a second reference electric energy larger than the first reference electric energy is used as the reference electric energy.

12. A non-combustion-type flavor inhaler having a shape extending from a non-mouthpiece end to a mouthpiece end in a predetermined direction, comprising:
an aerosol source generating aerosol;
an atomizer atomizing the aerosol source without combustion;
a power source supplying electric power to the atomizer;
a controller controlling an electric energy supplied from the power source to the atomizer;
wherein the controller randomly controls the electric energy supplied to the atomizer and increases the electric energy supplied to the atomizer from a reference electric energy in a stepwise manner in accordance with an increase of a number of times of puff actions of inhaling the aerosol, and
the controller randomly controls the reference electric energy.

13. The non-combustion-type flavor inhaler according to claim 12, wherein
in a case where the power source of the non-combustion-type flavor inhaler is deactivated in a first on-state where a power source of the non-combustion-type flavor inhaler is turned on, the controller randomly controls an electric energy supplied to the atomizer in a second on-state based on an electric energy that is supplied to the atomizer in the first on-state, the second on-state defined by a state where the power source of the non-combustion-type flavor inhaler is turned on again before a stationary time exceeds a predetermined stationary time, the stationary time defined by a time that is passed after deactivation of the power source of the non-combustion-type flavor inhaler.

14. The non-combustion-type flavor inhaler according to claim 13, wherein
a range of possible values for the electric energy supplied to the atomizer in the second on-state is narrower than a range of possible values for the electric energy to be supplied to the atomizer in the first on-state.

15. The non-combustion-type flavor inhaler according to claim 12, wherein
the controller controls: a standard mode applied to a user whose time required for one puff action of inhaling the aerosol is within a standard required time section period; and a shortening mode applied to a user whose time required for one puff action of inhaling the aerosol is shorter than the standard required time section period,
in one puff action in the standard mode, the controller controls the power source so as to supply a standard electric energy to the atomizer during a section before a first time is passed, and controls the power source so as to supply an electric energy smaller than the standard electric energy to the atomizer during a section after the first time is passed,
in one puff action in the shortening mode, the controller controls the power source so as to supply a first electric energy larger than the standard electric energy to the atomizer during a section before a second time is passed, controls the power source so as to supply a second electric energy smaller than the first electric energy to the atomizer during a section before a third time is passed after the second time, and controls the power source so as to supply an electric energy smaller than the second electric energy to the atomizer during a section after the third time is passed, and
the controller randomly controls the standard electric energy.

16. The non-combustion-type flavor inhaler according to claim 15, wherein
the controller sets the standard mode or the shortening mode based on learning of a puff action of a user.

17. The non-combustion-type flavor inhaler according to claim 12, wherein
the controller controls a first mode in which a first reference electric energy is used as the reference electric energy, and a second mode in which a second reference electric energy larger than the first reference electric energy is used as the reference electric energy.

18. The non-combustion-type flavor inhaler according to claim 12, wherein
the controller controls the power source so as to supply an electric energy smaller than the reference electric energy to the atomizer when the puff action is performed after a number of times of puff actions is exceeded a predetermined number of times.

19. The non-combustion-type flavor inhaler according to claim 18, wherein
the controller turns the power source of the non-combustion-type flavor inhaler off when a certain period of time is passed after the number of puff actions is exceeded a predetermined number of times.

20. The non-combustion-type flavor inhaler according to claim 12, wherein
the controller increases a gradient of the electric energy supplied to the atomizer in accordance with the increase of the number of times of puff actions of inhaling the aerosol.

* * * * *